United States Patent [19]

Katsumata et al.

[11] Patent Number: 4,710,471

[45] Date of Patent: Dec. 1, 1987

[54] NOVEL VECTOR PLASMIDS

[75] Inventors: Ryoichi Katsumata; Akio Ozaki, both of Mashida; Tetsuo Oka, Yokohama; Akira Furuya, Kawasaki, all of Japan

[73] Assignee: Kyowa Hakko Kogyo Co., Ltd., Tokyo, Japan

[21] Appl. No.: 668,674

[22] Filed: Nov. 5, 1984

Related U.S. Application Data

[63] Continuation of Ser. No. 450,359, Dec. 16, 1982, abandoned.

[30] Foreign Application Priority Data

Dec. 17, 1981 [JP] Japan .................................. 56-204319

[51] Int. Cl.⁴ .................... C12N 1/20; C12N 15/00; C12N 1/00
[52] U.S. Cl. ................................ 435/253; 435/172.3; 435/320; 935/29
[58] Field of Search ................ 435/172.3, 253, 317; 935/29

[56] References Cited

FOREIGN PATENT DOCUMENTS

| | | |
|---|---|---|
| 0063763 | 11/1982 | European Pat. Off. . |
| 0066129 | 12/1982 | European Pat. Off. . |
| 0071023 | 2/1983 | European Pat. Off. . |
| 0077548 | 4/1983 | European Pat. Off. . |
| 0088166 | 9/1983 | European Pat. Off. . |
| 0093611 | 11/1983 | European Pat. Off. . |
| 2482622 | 11/1981 | France . |
| 2076853 | 12/1981 | United Kingdom ............. 435/172.3 |

OTHER PUBLICATIONS

Kreft et al., Current Topics in Microbiology and Immunology, vol. 96, pp. 6-8, (1982).
Kaneko et al., Agric. Biol. Chem., vol. 43 (4), pp. 867-868, 1979.
Sakaguchi et al., Chemical Abstract, vol. 91 : 89549k 1979.
Goeddel et al., Nature, vol. 281, pp. 544-548, Oct. 18, 1979.

*Primary Examiner*—Alvin E. Tanenholtz
*Attorney, Agent, or Firm*—Fitzpatrick, Cella, Harper & Scinto

[57] ABSTRACT

Disclosed are recombinant plasmid vectors constructed of a plasmid autonomously replicable in cells of microorganisms belonging to the genus Corynebacterium or Brevibacterium and a DNA fragment containing a gene expressible by said microorganisms. The recombinant vector plasmids are autonomously replicable in glutamic acid—producing microorganisms and are useful to clone desired DNA fragments in such microorganisms.

9 Claims, 4 Drawing Figures

NOVEL VECTOR PLASMIDS

This application is a continuation of application Ser. No. 450,359, filed Dec. 16, 1982, now abandoned.

BACKGROUND OF THE INVENTION

The present invention relates generally to new vector plasmids and more specifically to a vector plasmid and the process for producing the same by inserting a DNA fragment containing a gene expressible in a microorganism belonging to the genus Corynebacterium or Brevibacterium into a plasmid derived from a microorganism belonging to the genus Corynebacterium or Brevibacterium. The resultant plasmid facilitates the cloning of desired genes in a host microorganism of the genus Corynebacterim or Brevibacterium.

With the advent of genetic engineering technology, it has become possible to insert a DNA fragment containing a desired gene into a vector such as plasmids and phages, and introduce the thus obtained recombinant DNA into a microbial cell whereby the microorganism inherits the gene by the help of autonomous replication of the vector.

Such technology was first established using *Escherichia coli* as a host microorganism. Thus, application of the technology to the production of useful metabolites by the fortification of the specific metabolic system and the production of useful proteins by the introduction of a gene derived from eucaryotes has been conducted using *Escherichia coli*.

Although the accumulated knowlege on *Escherichia coli* has greatly contributed to the progress of these researches, the successful development of useful vectors cannot be neglected. The importance of vectors in genetic engineering technology is clearly recognized in "Recombinant Molecules: Impact on Science and Society", Miles International Symposium Series No. 10, edited by R. F. Beers and E. G. Basset, Raven Press, New York, 1977.

Plasmid vectors are preferred in applied research using *Escherichia coli* as the host. A typical plasmid vector, pBR322, illustrates the advantages of plasmid vectors. For example pBR322 DNA can be readily recovered because of its replication characteristic of having many copies in a cell and a DNA fragment can be cloned in the plasmid without preventing the replication of pBR322 because of its small molecular weight and only one cleavage site for various restriction endonucleases. Moreover, genes responsible for ampicillin resistance and tetracycline resistance (hereinafter referred to as "Am ® gene" and "Tc ® gene" respectively) can be used as a marker to select a microorganism containing the plasmid.

The insertional inactivation is an additional advantage of pBR322. It has only one restriction site for each of PstI, BamHI, HindIII and SalI and the PstI site resides in the Am ® gene and the other three reside in the Tc ® gene. The insertion of a DNA fragment into these restriction sites will result in the loss of resistance due to the cleavage of the gene (insertional inactivation). Thus, it is possible to select a strain having a recombinant DNA by first selecting strains which are resistant to one of the drugs (Am or Tc) and then selecting those which become sensitive to the other drug due to the insertional inactivation, see, e.g., Bolivar, F. et al.: Gene, 2, 95 (1977).

A number of practical plasmid vectors for *Escherichia coli* have also been constructed which are similar to pBR322 in characteristics. For example, as a plasmid vector capable of the insertional inactivation of genes responsible for drug-resistance with more restriction endonucleases, plasmid pGA22 has been prepared. Since pGA22 has genes responsible for the resistance to chloramphenicol and kanamycin (hereinafter referred to as "Cm ® gene" and "Km ® gene" respectively) in addition to Am ® gene and Tc ® gene of pBR322, the insertional inactivation of Cm ® gene at EcoRI site and of Km ® gene at HindIII or XhoI site is possible as well as the insertional inactivation of Am ® gene and Tc ® gene See An. G. et al.: J. Bacteriol., 140, 400 (1979).

While, for industrially useful microorganisms other than *Escherichia coli*, such as amylase-producing Bacillus subtilis, antibiotics-producing Actinomycetes and alcohol-producing yeasts, recombinant DNA technology has been developed and vectors in these microorganisms have been obtained, examples of practical application of the technology using these organisms as a host are few. One of the reasons of such limited use is that in these microorganisms, a plasmid vector which is as useful as those of *Escherichia* coli has not been found. If *Escherichia coli* plasmids or fragments thereof are joined with plasmids for these organisms, they will automatically acquire the usefulness of the Escherichia coli plasmids described above. However, the successful use of drug resistance genes of *Escherichia coli* plasmids as vector markers has not been known in these other species. In this regard, it has been thought that although Gram positive Bacillus subtilis and Actinomycetes are procaryotes, genes of Gram negative Escherichia coli could not be expressed in these microorganisms. In fact, it has been reported that when a gene responsible for drug resistance of *Escherichia coli* used as a selection marker of an *Escherichra coli* vector plasmid is introduced into *Bacillus subtilis* or Actinomycetes after recombination with the plasmids of these microorganisms, the recombinant plasmid can replicate but the drug resistance gene can not be experessed, Kreft, J. et al.: Molec. Gen. Genet., 162. 59 (1978), Schottel, J. L. et al.: J. Bacteriol., 146, 360 (1981). Therefore, the results obtainable in Escherichia coli were not believed to be applicable directly to the above mentioned Gram positive microorganisms.

Thus, a need existed for application of the results of gene engineering technology in *Escherichia coli* to Gram positive microorganisms of the genera Corynebacterium and Brevibacterium in order to improve the efficient production of useful substances by these microorganisms. To this end, and in spite of the accepted theory that genes of Gram negative microorganisms are difficult to express in cells of Gram positive microorganisms, the present inventors have found that microorganisms of the genus Corynebacterium or Brevibacterium have an ability to express foreign genes of other microorganisms such as *Escherichia coli*.

SUMMARY OF THE INVENTION

In accordance with the present invention, useful plasmid vectors are provided for recombinant DNA technology using microorganisms of the genera Corynebacterium and Brevibacterium as host microorganisms. The main advantage of the present invention is in facilitating recombinant DNA technology in microorganisms of the genera Corynebacterium and Brevibacterium by inserting a gene expressible in cells of *Escher-* ichia coli into a plasmid autonomously replicable in cells of Corynebacterium and Brevibacterium to create selective markers and new cleavage sites for restriction endonucleases in the plasmid. The genes to be inserted into a plasmid include not only genes responsible for drug-resistance derived from an *Escherichia coli* plasmid and genes located on the chromosome of Escherichia coli, but also genes which are derived from microorganisms other than Escherichia coli. Recombinant plasmids wherein said genes are inserted into a plasmid of the genus Corynebacterium or Brevibacterium are constructed by conventional in vitro recombinant DNA technology and introduced into a microorganism of the genus Corynebacterium or Brevibacterium. Desired transformants are selected by the expression of the inserted genes, and the recombinant plasmids are recovered from cultured cells of the selected transformants.

DESCRIPTION OF THE INVENTION

Figure 1:
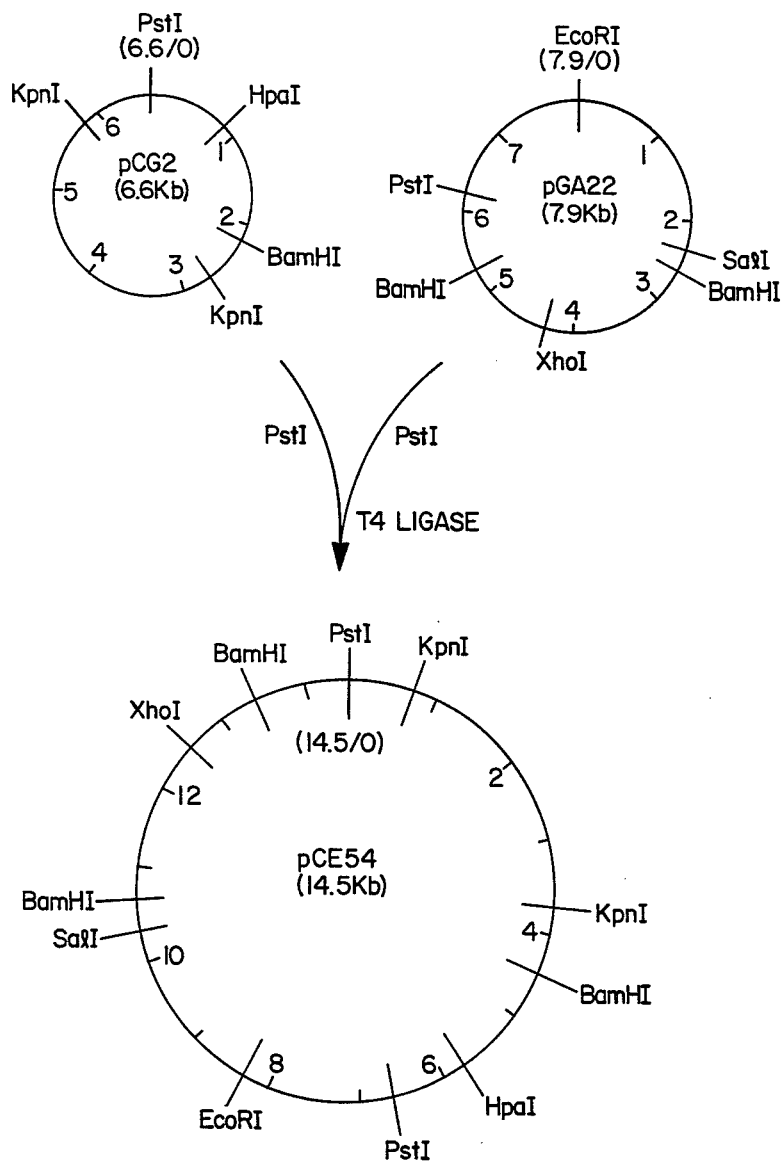
FIGS. 1, 2 and 3 llustrate respectively the processes for construction of and the cleavage maps for plasmids pCE54, pCB101 and pEthrl wherein "BGLII/Bam HI" with a broken line indicates a recombination site at the same cohesive ends formed by cleavage with both restriction endonucleases. The restriction endonucleases used in the preparation of the cleavage maps are PstI, KpnI, BamHI, HpaI, EcoRI, SalI and XhoI for plasmid pCE54, PstI, EcoRI, HincII and BglII for plasmid pCB101, and PstI, EcoRI and XhoI for plasmid pEthrl. Molecular weights of the plasmids are indicated as Kilobase (Kb)

The present invention provides a vector plasmid and a process for producing the same by inserting a DNA fragment containing a gene expressible in a microorganism belonging to the genus Corynebacterium or Brevibacterium into a plasmid autonomously replicable in cells of a microorganism of the genus Corynebacterium or Brevibacterium. The vector plasmid is autonomously replicable in a microorganism of such genera, the presence of which is detected by the expression of the inserted gene.

As genes expressible in a microorganism of the genus Corynebacterium or Brevibacterium, those derived from either eucaryotes or procaryotes may be employed. Preferably the genes responsible for drug resistance, the genes responsible for the biosynthesis of cell components such as amino acids, nucleic acids and vitamins, the genes responsible for the assimilation of substrates such as sugars, and the genes of plasmids and phages, derived from coryneform bacteria such as those of the genus Corynebacterium or Brevibacterium, bacteria belonging to the genera Escherichia, Microbacterium, Staphylococcus, Streptococcus, Pseudomonas, Serratia and Bacillus, yeasts and Actinomycetes are employed.

Examples of suitable plasmids and phages are pBR322, pBR325, pGA22, pACYC177, pACYC184, and λgtWESλB derived from microorganisms of the genus Escherichia, pUB110, pC194, pTP4 and φ11 derived from the genus Bacillus or Staphylococcus, pCG4 derived from the genus Corynebacterium or Brevibacterium, pSLP1. 2, pSLP111 and SCP2 derived from Actinomycetes and YEp13, YRp7 and YTp1 derived from yeasts.

As plasmids autonomously replicable in cells of the genus Corynebacterium or Brevibacterium, plasmids pCG1, pCG2, pCG4 and the like are preferably used. These plasmids are disclosed in Japanese patent application Nos. 18101/81, 133557/81 and 58186/81. Strains having these plasmids have been deposited with the American Type Culture Collection and the Fermentation Research Institute, Agency of Industrial Science and Technology under the accession numbers identified in the following Examples.

The recombinant plasmid vectors of the present invention include any recombinant plasmid vectors of two members selected from genes and plasmids which are obtained from mutually heteromicroorganisms, for example, a recombinant plasmid pCE54 wherein Escherichia coli plasmid pGA22 is combined with plasmid pCG2, a recombinant plasmid pCG11 wherein a part of plasmid pCG4 is combined with plasmid pCG1, a recombinant plasmid pCB101 wherein Staphylococcal plasmid pUB110 is combined with plasmid pCG11 and a recombinant plasmid pEthr1 wherein Escherichia coli plasmid pGH2 having threonine operon is combined with plasmid pCG11. Each of these plasmids is described more fully below.

Plasmid pCE54

To prepare plasmid pCE54, pCG2 is isolated from cultured cells of Corynebacterium glutamicum 225-218 by the method described in the aforementioned Japanese patent application, and set forth in Example 1 below, and plasmid pGA22 is isolated from cultured cells of Escherichia coli by a conventional manner. Both plasmid DNAs are linearized by complete digestion with a restriction enzyme which has only one cleavage site in each plasmid DNA, for example, PstI and treated with T4 phage DNA ligase to form composite molecules wherein cohesive ends of the DNAs are combined with each other. The desired recombinant plasmid which contains both DNAs are obtained by first selecting transformants of the genus Corynebacterium or Brevibacterium with respect to the drug-resistance derived from pGA22 and then analyzing plasmids in the transformants.

The transformation with the DNA mixture is carried out by the transformation method using protoplasts of cells of the genus Corynebacterium or Brevibacterium, which is described in Japanese patent application Nos. 58187/81 and 65777/81 by the present inventors, and described in the Example below. Drugs used for the selection are tetracycline, chloramphenicol and kanamycin, to which pGA22 carries drug resistant genes. Ampicillin cannot be used because Am ®️ gene is inactivated by the insertion of pCG2 at the PstI site. Transformants are recovered by isolating the colonies regenerating on a hypertensive agar medium containing a drug in a concentration wherein recipient protoplasts cannot be reversed to normal cells without addition of DNA, generally, 0.4 to 1.6 µg/ml tetracycline, 2.5 to 5 µg/ml chloramphenicol or 100 to 800 µg/ml kanamycin, or by collecting all the colonies regenerating unselectively on a regeneration medium and then isolating the desired colonies grown on an agar medium containing a drug in a concentration wherein normal cells cannot grow, generally, 0.5 to 4 µg/ml tetracycline, 2 to 15 µg/ml chloramphenicol or 2 to 25 µg/ml kanamycin.

Some of the transformants selected with respect to the resistance to tetracycline, chloramphenicol or kanamycin possess phenotypes of resistance to other drugs derived from pGA22.

Plasmid DNAs in the transformants can be isolated from cultured cells of the transformants by the method described in Japanese patent application Nos. 18101/81 and 65777/81 and in the Example below. Structures of the plasmid DNAs can be determined by analyzing the DNA fragments by agarose gel electrophoresis after digestion with various restriction enzymes. Plasmid pCE54 is isolated from one of the thus selected transformants. FIG. 1 illustrates the process for producting pCE54, and the cleavage map for various restriction endonucleases, which shows that pCE54 is a composite plasmid of pCG2 and pGA22 combined at their PstI cleavage sites. On the other hand, a composite plasmid of pCG2 and pGA22 wherein the direction of the combination is opposite to that of pCE54 is obtained from another transformant. Transformants resistant to the three drugs can be obtained by transforming microorganisms of the genus Corynebacterium or Brevibacterium with either of the composite plasmids and selecting the transformant in the same manner as described above. Further analysis confirms that these transformants have the same plasmid as the donor plasmid.

Sensitivity to tetracycline, chloramphenicol and kanamycin of Corynebacterium glutamicum LA103, a derivative of L-22, and a pCE54-containing strain thereof are illustrated in the following Table 1 as the minimum inhibitory concentration which prevents the growth of $10^4$ cells incubated on an NB agar medium (pH 7.2) consisting of 20 g/l powered bouillon, 5 g/l yeast extract and 18 g/l agar at 30° C. for 2 days.

TABLE 1

| Microorganism | Minimum inhibitory concentration (MIC, μg/ml) | | |
|---|---|---|---|
| | tetracycline | chloramphenicol | kanamycin |
| Corynebacterium glutamicum LA 103 | 0.8 | 1.6 | 0.8 |
| Corynebacterium glutamicum LA 103/pCE 54 | 3.2 | 12.5 | <400 |
| Corynebacterium glutamicum LA 103/pCB 101 | 0.8 | 1.6 | 200 |

As is apparent from the results shown in Table 1, the strain containing pCE54 expresses the resistance to the three drugs coded for by genes carried by pGA22. Therefore, pCE54 can be used as effectively in microorganisms of the genus Corynebacterium or Brevibacterium as pGA22 in Escherichia coli, to clone desired DNA fragments in these microorganisms.

Plasmid pCG11

Plasmid pCG11 is a plasmid invented by the present inventors and described in Japanese patent application No. 18101/81. Plasmid pCG11 is constructed by inserting a BamHI fragment of pCG4 isolated from *Corynebacterium glutamicum* 225-250 (ATCC 31830, FERM P-5939) carrying a gene responsible for the resistance to streptomycin and/or spectinomycin at the unique BglII site of pCG1 isolated from *Corynebacterium glutamicum* 225-57 (ATCC 31808, FERM P-5865).

Plasmid pCB101

As mentioned above, genes of *Escherichia coli* are not expressed in *Bacillus subtilis*. On the other hand, some of the genes expressed in microorganisms of the genus Bacillus are known to be expressed in *Escherichia coli*.

For example, it has been reported that when *Escherichia coli* is transformed with recombinant plasmids of a plasmid of Escherichia coli and a DNA carrying the genes responsible for drug resistance derived from either a plasmid or chromosome of Gram positive bacteria such as a Bacillus, these drug resistance genes are expressed. Ehrlich, S. D.: Proc. Natl. Acad. Sci., USA, 75, 1433 (1978); Kreft, J. et al.: Molec. Gen. Genet., 162. 59 (1978); and Gray, O. et al.: J. Bacteriol 145, 422 (1981). Therefore, genes of microorganisms other than *Escherichia coli* can be used to construct plasmid vectors for microorganisms of the genus Corynebacterium or Brevibacterium as useful as plasmid pCE54. A derivative plasmid wherein the characteristic of plasmid pUB110 is introduced is described below as an example of such plasmid vectors.

The plasmid pUB110 was originally isolated from a microorganism of the genus Staphylococcus resistant to kanamycin or neomycin. Plasmid pUB110 is employed as a vector in *Bacilllus subtilis* since it can replicate in *Bacillus subtilis* and its gene responsible for the resistance to kanamycin or neomycin can be expressed in *Bacillus subtilis*. See, e.g., Keggins, K. M. et al.: Proc. Natl. Acad. Sci. USA, 75, 1423 (1978). The expression of Km Ⓡ gene of pUB110 in *Escherichia coli* is confirmed by measuring the degree of resistance to kanamycin of an *Escherichia coli* strain containing a recombinant plasmid of pUB110 and an Escherichia coli plasmid prepared by recombinant DNA technology. More specifically, plasmid pUB110 and an *Escherichia coli* plasmid pBR325 (Bolivar, F. et al.: Gene, 4, 121, 1978) are each cleaved and ligated at the BamHI site to obtain two types of recombinant plasmids wherein the directions of combination are opposite to each other. The minimum inhibitory concentration of kanamycin is 50 μg/ml against *Escherichia coli* K-12 C 600 strains containing either type of the plasmid. Since the minimum inhibitory concentration of kanamycin against the C 600 strain which does not contain the plasmid is 1.6 μg/ml, it is apparent that the Km Ⓡ gene of pUB110 is expressed in Escherichia coli.

Plasmid pCB101 prepared by combining pUB110 and pCG11 is an example of application of the usefulness of pUB110 to plasmids for the genus Corynebacterium or Brevibacterium.

To prepare this plasmid, plasmid pCG11 isolated from *Corynebacterium glutamicum* LA 103 is digested with BglII and plasmid pUB110 isolated from *Bacillus subtilis* is digested with BamHI to linearize them. Since both plasmids have the same cohesive ends due to the cleavage specificity of BglII and BamHI, treatment of the mixture of the two digests with T4 phage ligase gives various recombinant plasmids formed through the complementary base pairing with the cohesive ends. The mixture is used to transform the protoplast of Corynebacterium glutamicum LA 103. Transformants can be selected with respect to the resistance to kanamycin derived from pUB110 in the same manner as in the selection of pCE54. Some transformants resistant to kanamycin also obtain simultaneously the spectinomycin resistance encoded for by pCG11.

Figure 2:
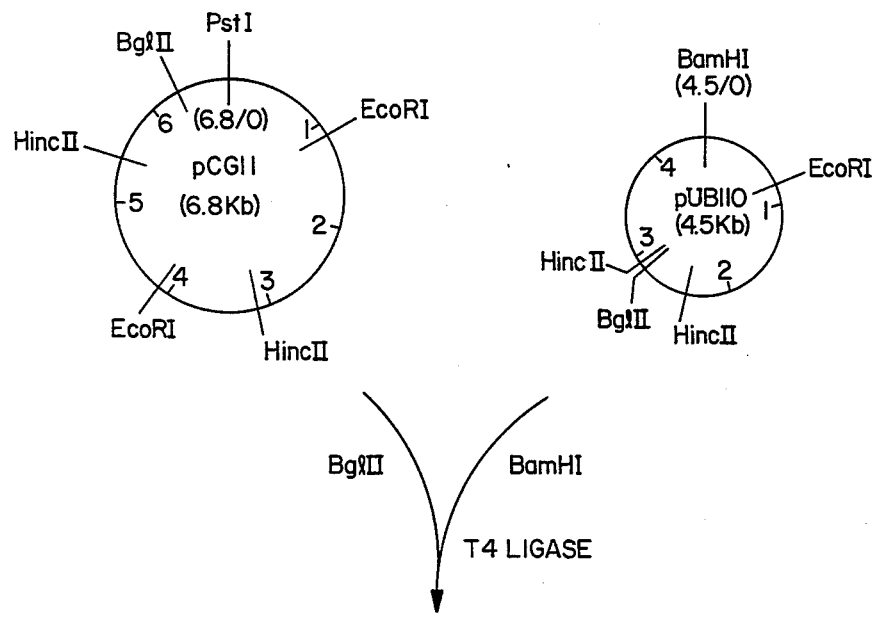
Figure 2:
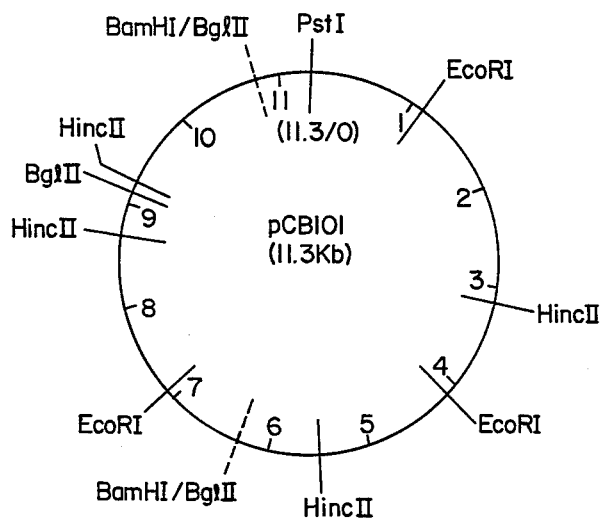

The structure of the plasmid DNA in the strain resistant to both kanamycin and spectinomycin is determined by digesting the plasmid DNA with various restriction endonucleases and analyzing the fragments by agarose gel electrophoresis. Plasmid pCB101 is a plasmid isolated from one of the transformants. The process for producing pCB101 and the cleavage map thereof are illustrated in FIG. 2. As is apparent from FIG. 2, pCB101 is a composite plasmid wherein BglII-opened pCG11 is inserted at the BamHI site of pUB110. Another transformant gives a composite plasmid wherein the orientation of the insertion of pCG11 and pUB110 is opposite to that of pCB101. When either composite plasmid is introduced into *Corynebacterium glutamicum* LA 103 in the same manner as mentioned above and transformants are selected with kanamycin or spectinomycin, the transformants also gain resistance to the other drug which is not used for selection and have the same plasmids as donor plasmids characterized by cleavage sites for various restriction endonucleases.

The minimum inhibitory concentrations of kanamycin against *Corynebacterium glutamicum* LA 103 with or without pCB101 are also illustrated in Table 1 above. As is apparent from Table 1, the strain with pCB101 expresses not only the spectinomycin resistance gene derived from pCG11, but also the Km ® gene derived from pUB110. Thus pCB101 has two drug-resistance genes which can serve as selective markers in microorganisms of the genus Corynebacterium or Brevibacterium. In addition, pCB101 can facilitate cloning of desired DNA fragments in these microorganisms by insertional inactivation since there is a BglII site in the Km ® gene in pUB110. Gryczan, T. et al.: J. Bacteriol., 141, 246 (1980).

Plasmid pEthr1

As noted above, it is possible to make plasmids of microorganisms of the genus Corynebacterium or Brevibacterium more useful by attaching the drug resistance genes expressible in Escherichia coli as vector markers. Useful plasmid vectors can also be prepared by inserting chromosomal genes expressible in *Escherichia coli*, for example, genes responsible for a metabolic function. Since the role of a vector marker is to facilitate the selection of a strain having recombinants, when the host microorganism is a mutant lacking a certain phenotype, a plasmid having a chromosomal gene of a wild type will serve as a useful vector with a selection marker in the mutant.

Plasmid vectors carrying chromosomal genes as selection markers in Corynebacterium or Brevibacterium can be constructed by conventional in vitro recombinant DNA technology as described above. More specifically, a fragment of chromosomal DNA extracted from a microorganism or a DNA fragment cloned in an *Escherichia coli* vector is inserted in vitro in a plasmid of a microorganism of the genus Corynebacterium or Brevibacterium to make a recombinant plasmid. Then, a mutant strain belonging to the genus Corynebacterium or Brevibacterium and lacking a particular phenotype is transformed with the recombinant plasmid, followed by slection of a transformant wherein the lost phenotype is complemented. A mutant lacking a particular phenotype can be obtained by a conventional mutation method.

For example, a derivative plasmid wherein a DNA fragment containing an *Escherichia coli* threonine operon is inserted in a plasmid of a microorganism of the genus Corynebacterium is used as a vector in a host microorganism belonging to *Corynebacterium glutamicum* and requiring homoserine or methionine plus threonine. The threonine operon of Escherichia coli in the plasmid can serve as a selection marker because the requirement for homoserine due to the lack or homoserine dehydrogenase in the host strain is complemented with the homoserine dehydrogenase gene coded in the threonine operon of Escherichia coli.

A plasmid, pEthr1, containing a threonine operon of *Escherichia coli* is explained below.

A DNA fragment containing a threonine operon of *Escherichia coli* is cloned using a host-vector system of *Escherichia coli*. A chromosomal DNA extracted from an *Escherichia coli* strain having a wild type threonine operon and an *Escherichia coli* vector plasmid pGA22 are digested with a restriction endonuclease, HindIII. The mixture of the two digests is treated with T4 phage ligase. *Escherichia coli* K-12, GT-3 requiring homoserine and diaminopimelic acid is transformed with the mixture in a conventional manner and transformants grown on a minimum medium containing kanamycin and diaminopimelic acid are selected. Plasmids in the transformants are isolated from cultured cells in a conventional manner and the structure is determined by analyzing DNA fragments formed by digestion with various restriction endonucleases by agarose gel electrophoresis. One of the thus obtained plasmids is pGH2 illustrated in FIG. 3. A DNA fragment containing an *Escherichia coli* threonine operon has already been cloned and the cleavage map was determined. Cossart, P. et al.: Molec. Gen. Genet., 175, 39 (1979). It is certain that pGH2 has a threonine operon because the inserted fragment has the same restriction map as that of Escherichia coli threonine operon.

Figure 3:
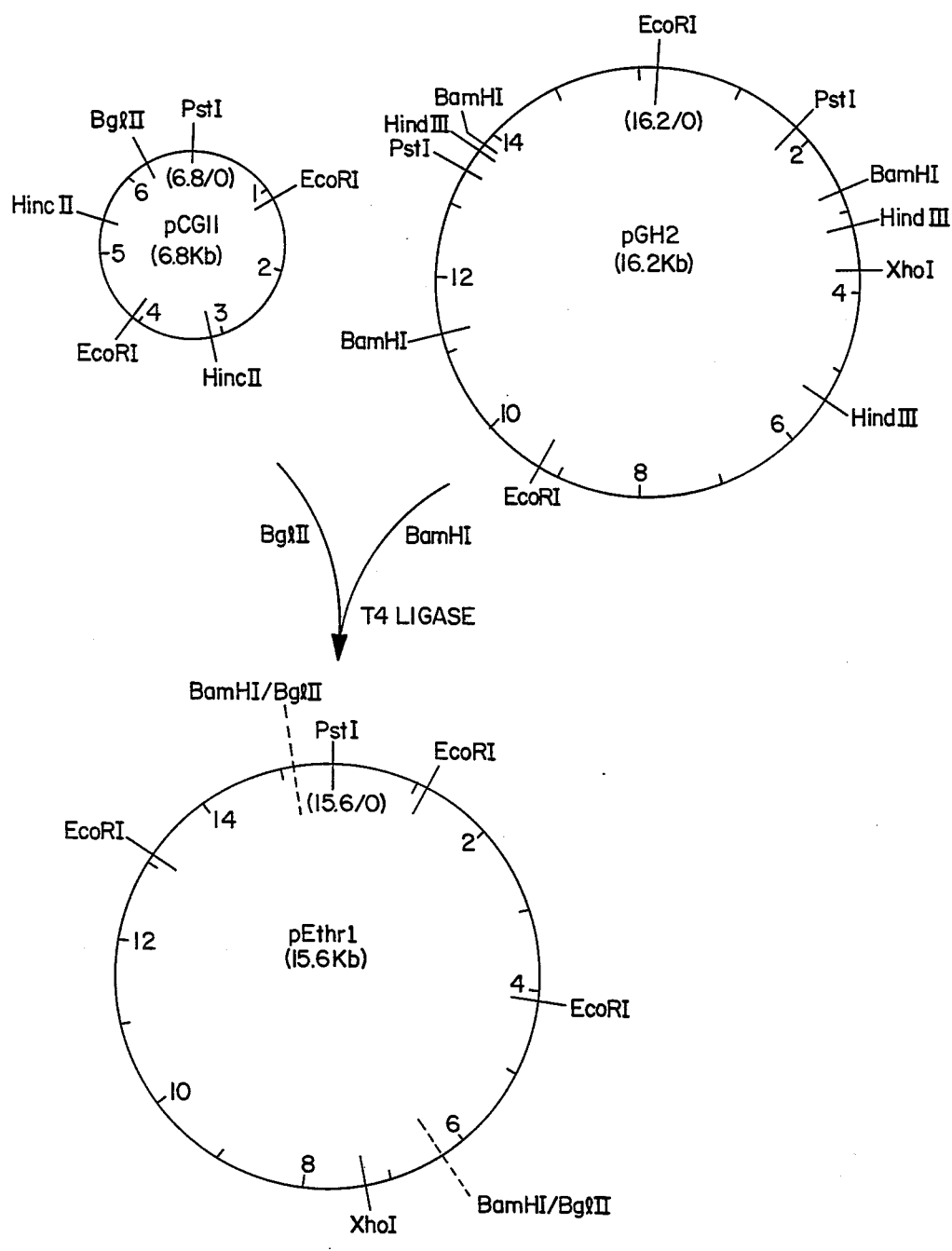

Plasmid pEthr1 is constructed as a recombinant of pGH2 and pCG11. Plasmid pGH2 is digested with BamHI and pCG11 is digested with BglII in a conventional manner. The mixture of the digests is treated with T4 ligase. Protoplasts of Corynebacterium glutamicum LA 201, a mutant requiring homoserine and leucine and derived from an L-22 strain, are transformed with the mixture in the same manner as described above. The protoplasts are unselectively regenerated on a regeneration medium. Then, the regenerated cells are collected and spread on a minimum medium containing leucine and the formed colonies are recovered. Some of the thus obtained strains which do not require homoserine have both phenotypes of kanamycin-resistance derived from pGH2 and that of spectinomycin-resistance derived from pCG11. Plasmid pEthr1 is a plasmid isolated from one of such transformants. The process for the construction of pEthr1 and the cleavage map of pEthr1 based upon analysis by agarose gel electrophoresis after digestion with various endonucleases are illustrated in FIG. 3. It is apparent from FIG. 3 that pEthr1 is a plasmid wherein a fragment containing a threonine operon of pGH2 cleaved with BamHI is inserted in pCG11. From another transformant, a plasmid wherein the orientation of the BamHI fragment of pGH2 is opposite to that in pEthr1 is obtained. The threonine operon inserted at either orientation can complement homserine-requirement in *Corynebacterium glutamicum* LA 201 which has become resistant to kanamycin and spectinomycin. The thus obtained transformants have the donor plasmid characterized by the cleavage sites for various restriction endonucleases. Therefore, pEthr1 is a plasmid which facilitates cloning of DNA fragments in *Corynebacterium glutamicum* LA 201 because the homoserine dehydrogenase gene on the threonine operon derived from *Eschericia coli* serves as a selection marker.

The thus prepared plasmids for Corynebacterium or Brevibacterium containing a selection marker can be used as a vector for cloning a DNA fragment carrying desired genes in a host microorganism belonging to the genus Corynebacterium or Brevibacterium. Cloning is carried out by recombining a donor DNA and a vector plasmid by in vitro DNA recombination technology and transforming the microorganism of the genus Corynebacterium or Brevibacterium with the recombinant plasmid in a conventional manner as described above. Especially, when the donor DNA is inserted into a cleavage site present in the gene introduced as a vector marker, the desired recombinants are easily selected by checking the loss of phenotypic expression of the gene in the transformants.

The above-described plasmids pCE54, pCG11, pCB101 and pEthr1 introduced in *Corynebacterium glutamicum* LA 103 or LA 201 have been deposited with the American Type Culture Collection, U.S.A., under the accession numbers set forth in Table 2.

TABLE 2

| Strain (host microorganism/plasmid) | ATCC No. |
|---|---|
| *Corynebacterium Glutamicum* LA103/pCE54 | 39019 |
| *Corynebacterium Glutamicum* LA103/pCG11 | 39022 |
| *Corynebacterium Glutamicum* LA103/pCB101 | 39020 |
| *Corynebacterium Glutamicum* LA201/pEthr1 | 39021 |

In these plasmids, the *Escherichia coli* gene or the gene expressible in cells of *Escherichia coli* is merely inserted into the plasmid of *Corynebacterium glutamicum* without using any special technique for expression. As the genes of the DNA fragments inserted at any orientation into the plasmid of *Corynebacterium glutamicum* are expressed in *Corynebacterium glutamicum*, it is apparent that *Corynebaterium glutamicum* has the ability to recognize precisely the initiation signals for transcription and translation of the introduced gene to accomplish the transcription and translation. In view of the presence of common base sequences required for precise transcription and translation of *Escherichia coli* genes, Corynebacterium is considered to be able to recognize the initiation sites for transcription and translation of *Escherichia coli* genes other than those described above and to express such genes. Therefore, any gene expressible in *Escherichia coli* can be introduced as a marker into the plasmids of the present invention.

Since the usefulness of the present invention is the provision of a vector plasmid for microorganisms of the genus Corynebacterium or Brevibacterium having a selection marker, the purpose of the present invention is achieved by inserting a marker gene into a plasmid of a microorganism of the genus Corynebacterium or Brevibacterium in such a way as to be expressed. Therefore, for those genes described herein it should be understood that the method of inserting the genes into the plasmids of Corynebacterim glutamicum is not restricted to those described in the following examples. Moreover, since any plasmid autonomously replicable in microorganisms of the genus Corynebacterium or Brevibacterium can be used to make a plasmid having a selection marker by inserting a gene expressible in Escherichia coli, it will be appreciated that suitable plasmids of microorganisms of the genus Corynebacterium or Brevibacterium are not restricted to those described in the present specification.

In spite of many common microbial properties, microorganisms with high glutamic acid productivity (so called glutamic acid-producing microorganisms) are classified to various species and even genera such as Corynebacterium and Brevibacterium probably because of their industrial importance. However, it has been pointed out that these microorganisms should be classified as one species because they have homology in the amino acids in the cell walls and the GC content of DNA. Recently, it has been reported that these microorganisms have more than 70% homology in DNA, indicating that the microorganisms are very closely related. Komastsu, Y.: Report of the Fermentative Research Institute, No. 55, 1 (1980), and Suzuki, K., Kaneko, T., and Komagata, K.: Int. J. Syst. Bacteriol., 31, 131 (1981).

In the present specification, the usefulness of the plasmids of the present invention is illustrated using derivatives of Corynebacterium glutamicum L-22 as host microorganisms because of regulations on experiments using recombinant DNA technology. However, considering the above-mentioned relation of glutamic acid-producing microorganisms, it is apparent that the plasmids of the present invention are applicable to all of the glutamic acid-producing microorganisms. In order to use the plasmid as a vector in these microorganisms, slight differences in the properties of host microorganisms such as homology of the DNA is negligible and it is sufficient that these microorganisms have functions for the autonomous replication of the plasmids and the expression of introduced genes. It is apparent that these microorganisms have such functions from the fact that plasmid pCG4, which is isolated from *Corynebacterium glutamicum* 225-250, and has a streptomycin and/or spectinomycin resistance gene can replicate in other glutamic acid-producing microorganisms belonging to the genus Corynebacterium or Brevibacterium and the streptomycin and/or spectinomycin resistance gene can be expressed. Therefore, the host of the plasmids of the present invention is not limited to Corynebacterium glutamicum but includes all of the glutamic acid-producing microorganisms including those microorganisms belonging to the genus Corynebacterium or Brevibacterium.

Certain specific embodiments of the present invention are illustrated by the following representative examples.

EXAMPLE 1

Preparatron of plasmid pCE54

(1) Isolation of pCG2 and pGA22:

*Corynebacterium glutamicum* 225-218 strain (FERM P-5954, ATCC 31832) is cultured with shaking at 30° C. for 18 hours in NB medium (pH 7.2) consisting of 20 g/l powdered bouillon and 5 g/l yeast extract. Then, 5 ml of the culture is inoculated in 400 ml of a semisynthetic medium SSM (pH 7.2) consisting of 20 g/l glucose, 10 g/l (NH$_4$)$_2$ SO$_4$, 3 g/l urea, 1 g/l yeast extract, 1 g/l KH$_2$PO$_4$, 0.4 g/l MgCl$_2$6H$_2$O, 10 mg/l FeSO$_4$ . 7H$_2$O, 0.2 mg/l MnSO$_4$. (4–6) H$_2$O, 0.9 mg/l ZnSO$_4$ . 7H$_2$O, 0.4 mg/l CuSO$_4$.5H$_2$O, 0.09 mg/l Na$_2$B$_4$O$_7$10H$_2$O, 0.04 mg/l (NH$_4$)$_6$Mo$_7$O$_{24}$. 4H$_2$O, 30 μg/l biotin and 1 mg/l thiamine. HCl and culturing is carried out with shaking at 30° C. The optical density (OD) of the culture medium is measured at 660 nm with a Tokyo Koden Colorimeter and at an OD value of 0.2, penicillin G is added to a concentration of 0.5 U/ml. Culturing is continued at 30° C. to an OD value of about 0.6.

Cells are recovered from the culture medium and washed with TES buffer solution (pH 8.0) consisting of 0.03M tris (hydroxymethyl) aminomethane (referred to as "Tris" hereinafter), 0.005M EDTA, and 0.05M NaCl. The washed cells are suspended in a lysozyme solution (pH 8.0) consisting of 25% sucrose, 0.1M NaCl, 0.05M Tris and 0.8 mg/ml lysozyme to make 10 ml of a suspension. The suspension is allowed to react at 37° C. for 4 hours. Then, 2.4 ml of 5M NaCl, 0.6 ml of 0.5M EDTA (pH 8.5) and 4.4 ml of 4% sodium lauryl sulfate and 0.7M NaCl solutions are added to the suspension successively. The mixture is shaken slowly and put on an ice water for 15 hours. The whole lystate is then transferred into a centrifugation tube and centrifuged at 4° C. at 69, 400×g for 60 minutes to recover the supernatant fluid. Polyethyleneglycol (PEG 6000) (product of Nakarai Kagaku Yakuhin Co.) is added to 10% by weight, and the mixture is shaken slowly and put on an ice water for 10 hours. The mixture is then centrifuged at 1,500×g for 10 minutes to recover a pellet. The pellet is dissolved gently in 5 ml of TES buffer solution. Then, 2.0 ml of 1.5 mg/ml ethidium bromide solution, is added and thereafter cesium chloride is added to adjust the density to 1.580. The solution is subjected to density gradient centrifugation at 105,000×g at 18° C. for 48 hours. A covalently closed circular DNA is detected by UV irradiation as a high density band located in the lower part of the centrifugation tube. The band is taken out from the side of the centrifugation tube with a syringe to obtain a fraction containing plasmid pCG2. Then, the fraction is treated five times with an equal amount of cesium chloride staturated isopropyl alcohol solution consisting of 90% by volume isopropyl alcohol and 10% TES buffer solution to extract and remove ethidium bromide. The residue is subjected to dialysis against TES buffer solution to obtain 40 μg of pCG2 plasmid DNA.

Plasmid pGA22 is isolated from cultured cells of an *Escherichia coli* K-12 derivative, prepared by An, G. et al. according to the method of An, et al. J. Bacteriol, 140, 400 (1979).

(2) In vitro recombination of pCG2 and pGA22

4 units of PstI (product of Takara Shuzo Co., 6 units/μl ) is added to 200 μl of a restriction endonuclease reaction solution consisting of 20 mM Tris-HCl, 10 mM MgCl$_2$, 50 mM (NH$_4$)$_2$SO$_4$, 0.01% bovine serum albumin (pH 7.5) and 2 μg each of pCG2 and pGA22 plasmid DNAs prepared as above. The mixture is allowed to react at 30° C. for 60 minutes and then heated at 65° C. for 10 minutes to stop the reaction. The linearization of both circular plasmids is confirmed by analyzing the sample treated in the same manner by horizontal 0.8% agarose gel electrophoresis containing 0.6 μg/ml ethidium bromide.

Thereafter, 40 μl of T4 ligase buffer solution (pH 7.6) consisting of 660 mM Tris, 66 mM MgCl$_2$ and 100 mM dithiothreitol, 40 μl of 5 mM ATP, 0.2 μl of T4 ligase (product of Takara Shuzo Co., 1 unit/μl ) and 120 μl of H$_2$O are added to 200 μl of the reaction mixture. The mixture is allowed to react at 12° C. for 16 hours and extracted twice with 400 μl of phenol saturated with TES buffer solution. The residue is subjected to dialysis against TES buffer solution to remove phenol.

(3) Recovery of pCE54

Transformation is carried out using the protoplast of recipient cells. A seed culture of Corynebacterium glutamicum LA 103 is inoculated in the NB medium and cultured with shaking at 30° C. Cultured cells are collected at an OD value of 0.6 and suspended in an RCGP medium (pH 7.6) containing 1 mg/ml lysozyme at a concentration of about 10$^9$ cells/ml. The RCGP medium consists of 5 g/l glucose, 5 g/l casamino acid, 2.5 g/l yeast extract, 3.5 g/l K$_2$HPO$_4$, 1.5 g/l KH$_2$PO$_4$, 0.14 g/l MgCl$_2$6H$_2$O, 10 mg/l FeSO$_4$ . 7H$_2$O, 2 mg/l MnSO$_4$(4–6) H$_2$O, 0.9 mg/l ZnSO$_4$ 7H$_2$O, 0.04 mg/l (NH$_4$)$_6$Mo. 7O$_{24}$ 4H$_2$O, 30 μg/l biotin, 2 mg/l thiamine hydrochloride, 135 g/l sodium succinate and 30 g/l polyvinylpyrrolidone of a molecular weight of 10,000. The suspension is put into an L-tube and allowed to react with gentle shaking at 30° C. for 5 hours to make protoplasts.

Then, 0.5 ml of the protoplast suspension is transferred into a small tube and subjected to centrifugation at 2,500×g for 5 minutes. The residue is resuspended in 1 ml of a TSMC buffer solution (pH 7.5) consisting of 10 mM magnesium chloride, 30 mM calcium chloride, 50 mM Tris and 400 mM sucrose and subjected to centrifugation and washing. The residue is resuspended in 0.1 ml of the TSMC buffer solution. Then, 100 μl of a mixture of a two-fold concentrated TSMC buffer solution and the above-described DNA mixture treated with ligase (1:1) is added to the suspension and 0.8 ml of a TSMC buffer solution containing 20% PEG 6,000 is added. After 3 minutes, 2 ml of the RCGP medium (pH 7.2) is added and the mixture is subjected to centrifugation at 2,500×g for 5 minutes. The supernatant fluid is removed and the precipitated protoplasts are suspended in 1 ml of the RCGP medium. The suspension is slowly shaken at 30° C. for 2 hours to express the gene. Thereafter, a suitable amount of the protoplast suspension is spread on an RCGP agar medium (pH 7.2) containing 400 μg/ml kanamycin and 1.4% agar and cultured at 30° C. for 6 days.

Five of the kanamycin-resistant transformants are selected at random and purified on NB agar medium containing 12.5 μg/ml kanamycin. The thus purified five strains are propagated in 400 ml of the NB medium to an OD value of about 0.8 and then cells are collected. Plasmids are isolated from the cells by the same process as described in process (1) to isolate pCG2. About 45–55 μg of plasmid DNA is obtained from each transformant. Then, 0.5 μg of the plasmid DNA is single- or double-digested with various restriction endonucleases and the DNA fragments formed are analyzed by agarose gel electrophoresis to determine the molecular weights of the fragments and the cleavage sites in the plasmid molecules. Restriction endonucleases such as HpaI, PstI, KpnI, BamHI, EcoRI, SalI and XhoI (HpaI is a product of Boehringer Mannheim GmbH and the other enzymes are products of Takara Shuzo Co.) are used. The molecular weight is determined by reference to the standard curve plotted with electrophoretic distances of the HindIII fragments of known molecular weight derived from λphage DNA. All of the five plasmids have the structure of a composite plasmid of pCG2 and pGA22. Two of them have the structure illustrated as pCE54 in FIG. 1 and the others have a structure wherein the orientation of the combination of pCG2 with pGA22 is opposite. Transformants having either of the plasmids are endowed with resistance to tetracycline, chloramphenicol and kanamycin derived from pGA22 as is the case shown in Table 1.

*Corynebacterium glutamicum* LA 103 transformed with these plasmid DNAs by the same method as described above is also endowed with resistance to the three drugs and has the same plasmid as the donor plasmid identified by the cleavage pattern for various restriction endonucleases.

Example 2

Preparation of plasmid pCG11

Plasmid pCG1 is isolated from *Corynebacterium glutamicum* 225-57 by the method used for the isolation of pCG4 from *Corynebacterium glutamicum* 225-250. Plasmid pCG1 is completely digested with BglII which is a restriction endonuclease derived from *Bacillus globigii* (product of Takara Shuzo Co.) and plasmid pCG4 is completely digested with BamHI (product of Takara Shuzo Co.) under suitable conditions for each restriction endonuclease. Then, 0.1 unit of T4 phage DNA ligase (product of Takara Shuzo Co.) is mixed with 0.2 ml of a ligase reaction solution (pH 7.6) consisting of 66 mM Tris-HCl, 6.6 mM MgCl$_2$, 10 mM dithiothreitol and 0.5 mM ATP and containing 0.5 µg each of both digests and the mixture is allowed to react at 4° C. overnight. The protoplast of *Corynebacterium glutamicum* LA 103 strain is transformed with the ligation mixture.

Figure 4:
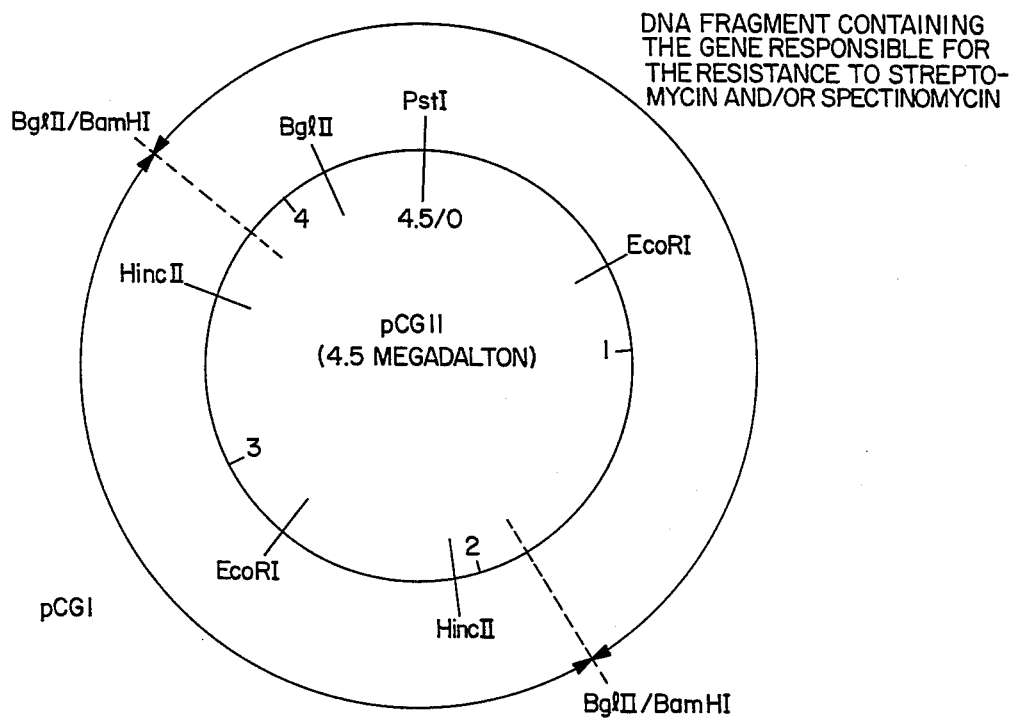
FIG. 4 illustrates the cleavage map of plasmid pCGll.

The protoplast of *Corynebacterium glutamicum* LA 103 strain is prepared as in Example 1. The transformation and selection of transformants are carried out by the same method as in Example 1. For transformation, 0.1 ml of the reaction mixture is used. Then, 50 µg of a plasmid DNA is isolated from one of the spectinomycin-resistant transformants by the same method as in Example 1. The plasmid DNA is subjected to single and double digestion with various restriction endonucleases. The resultant DNA fragments are analyzed by the same agarose gel electrophoresis as in Example 1 to determine the molecular weight and the cleavage sites in the plasmid molecule. The cleavage map of plasmid pCG11 is illustrated in FIG. 4.

*Corynebacterium glutamicum* LA 103 is transformed with pCG11 plasmid DNA in the same manner as above. The resultant spectinomycin-resistant strain has a plasmid characterized by the same cleavage pattern as that of pCG11.

EXAMPLE 3

Preparation of plasmid pCB101

(1) Isolation of pCG11 and pUB110:

*Corynebacterium glutamicum* LA 103/pCG11 (ATCC 39022) is grown in 400 ml of NB medium to an OD value of about 0.8 and pCG11 is isolated from the cultured cells by the same method as in the isolation of pCG2 in Example 1 (1).

Plasmid pUB110 is isolated from cultured cells of *Bacillis subtilis* BR 151/pUB110 (Proc. Natl. Acad. Sci. USA, 75, 1423, 1978) by the method of Gryczan, et al. Gryczan, T. J., et al.: J. Bacteriol., 134, 318 (1978).

(2) In vitro recombination of pCG11 and pUB110:

2 units of BglII (product of Takara Shuzo Co., 6 units/µl) is added to 100 µl of the BglII reaction buffer solution (pH 7.5) consisting of 10 mM Tris-HCl, 7 mM MgCl$_2$, 60 mM NaCl and 7 mM 2-mercaptoethanol and containing 2 µg of pCG11 plasmid DNA prepared as above. The mixture is allowed to react at 37° C. for 60 minutes. Separately, 2 units of BamHI (product of Takara Shuzo Co., 6 units/µl) is added to 100 µl of BamHI reaction buffer solution (pH 8.0) consisting of 10 mM Tris-HCl, 7 mM MgCl$_2$, 100 mM NaCl, 2 mM mercaptoethanol and 0.01% bovine serum albumin and containing 2 µg of pUB110 plasmid DNA. The mixture is allowed to react at 37° C. for 60 minutes.

Both digests are mixed and 40 µl of the T4 ligase buffer solution, 40 µl of ATP (5 mM), 0.2 µl of T4 ligase and 120 µl of H$_2$O are added. The mixture is allowed to react at 12° C. for 16 hours. The mixture is then extracted twice with 400 µl of pheonol saturated with TES buffer solution and the extract is subjected to dialysis against TES buffer solution to remove pheonol.

(3) Recovery of plasmid pCB101:

*Corynebacterium glutamicum* LA 103 is transformed using 100 µl of a mixture (1:1) of a two-fold concentrated TSMC buffer solution and the ligase reaction mixture mentioned above as a donor DNA in the same manner as in Example 1 (3) and kanamycin-resistant strains are selected. The formed colonies are replicaplated to an NB agar medium containing 12.5 µg/ml kanamycin and 100 µg/ml spectinomycin. Culturing is carried out at 30° C. for 2 days. Three strains resistant to both drugs are selected at random and purified on the same agar medium. The three purified strains are then grown in 400 µl of the NB medium to an OD value of about 0.8. Cells are recovered and the plasmids are isolated from the cells by ethidium bromide-cesium chloride density gradient centifugation described in Example 1 (1) whereby 30–35 µg of plasmid DNA is obtained from each transformant.

These plasmid DNAs are digested with restriction endonuclease and analyzed by agarose gel electrophoresis as in Example 1 (3) to determine the molecular weights and cleavage map for restriction endonucleases PstI, EcoRI, HincII and BglII. The plasmids of the three strains have the structure of a composite plasmid of pCG11 and pUB110. Two of them have the structure illustrated as pCB101 in FIG. 2 and the other has the structure wherein the orientation of the combination of pCG11 and pUB101 is opposite.

Transformants having either of the plasmids are endowed with the phenotype of resistance to spectinomycin derived from pCG11 and that of resistance to kanamycin from pUB110.

*Corynebacterium glutamicum* LA 103 is retransformed with these plasmid DNAs. The resultant kanamycin-resistant transformant is endowed simultaneously with the phenotype of resistance to spectinomycin. It has the same plasmid as the donor plasmid as characterized by the cleavage pattern for various restriction endonucleases.

EXAMPLE 4

Preparation of plasmid pEthrl (1) Cloning of a DNA fragment containing *Escherichia coli* threonine operon:

Cloning is carried out using a host-vector system of *Escherichia coli*. Plasmid pGA22, used as a vector, is isolated as in Example 1 (1). A high molecular weight chromosomal DNA used as a donor DNA is isolated from cultured cells of *Escherichia coli* K 12 Hfr (ATCC 23740) by the phenol-extraction method of Smith, M. G.: Method in Enzymology, 12, part A, 545 (1967). Then, 0.4 unit of HindIII (product of Takara Shuzo Co., 6 units/µl) is added to 60 µl of a HindIII reaction solution (pH 7.5) consisting of 10 mM Tris-HCl, 7 mM MgCl$_2$ and 60 mM NaCl and containing 4 µg of pGA22 plasmid DNA. The mixture is allowed to react at 37° C. for 30 minutes and heated at 65° C. for 10 minutes to stop the reaction. pGA22 plasmid DNA is digested with HindIII under the same conditions as above and subjected to agarose gel electrophoresis. It is confirmed that one of the two HindIII cleavage sites present in pGA22 is cleaved.

Separately, 4 units of HindIII is added to 140 μl of the HindIII reaction solution containing 8 μg of the chromosomal DNA. The mixture is allowed to react at 37° C. for 60 minutes and heated at 65° C. for 10 minutes to stop the reaction.

Then, 40 μl of the T4 ligase buffer solution, 40 μl of ATP (5 mM), 0.3 μl of T4 ligase and 120 μl of H₂O are added to a mixture of the digests and reaction is carried out at 12° C. for 16 hours. The reaction mixture is extracted twice with 400 μl of phenol saturated with TES buffer solution and subjected to dialysis against TES buffer solution to remove phenol.

The ligase reaction mixture is used to transform *Escherichia coli* GT-3 (J. Bacteriol. 117, 133-143, 1974) which is a derivative of *Escherichia coli* K-12 and requires homoserine and diaminopimelic acid. Competent cells of the GT-3 strain are prepared according to the method of Dagert, M. et al., Gene, 6, 23 (1979). That is, the strain is inoculated in 50 ml of L-medium (pH 7.2) consisting of 10 g/l Bacto-tryptone, 5 g/l yeast extract, 1 g/l glucose and 5 g/l sodium chloride and containing 100 μg/ml diaminopimelic acid and cultured at 37° C. to an OD value of 0.5. The culture is cooled with ice water for 10 minutes and cells are recovered by centrifugation. The cells are suspended in 20 ml of cooled 0.1M calcium chloride. The suspension is allowed to stand at 0° C. for 20 minutes and then subjected to centrifugation to recover the cells. The cells are suspended in 0.5 ml of 0.1M calcium chloride and allowed to stand at 0° C. for 18 hours. Then 200 μl of the ligase reaction mixture mentioned above is added to 400 μl of the cell suspension treated with calcium chloride. The mixture is allowed to stand at 0° C. for 10 minutes and then heated at 37° C. for 5 minutes. Thereafter, 9 ml of the L-medium is added and the mixture is incubated with shaking at 37° C. for 2 hours. Cells are recovered by centrifugation and washed with a physiological saline solution twice. The cells are spread on M9 minimum agar medium (pH 7.2) consisting of 2 g/l glucose, 1 g/l NH₄Cl, 6 g/l Na₂HPO₄, 3 g/l KH₂PO₄, 0.1 g/l MgSO₄. 7H₂O, 15 mg/l CaCl₂. 2H₂O, 4 mg/l thiamine hydrochloride and 15 g/l agar and containing 12.5 μg/ml kanamycin. Culturing is carried out at 37° C. for 3 days. Only one colony is formed and the cells of such colony can also grow on an L-agar medium containing 25 μg/ml ampicillin, 25 μg/ml chloramphenicol or 25 μg/ml kanamycin.

A plasmid DNA is isolated from cultured cells of the transformant by the same method as in the isolation of pGA22 in Example 1 (1). The plasmid DNA is digested with restriction endonucleases and analyzed by agarose gel electrophoresis. The plasmid DNA has the structure illustrated as pGH2 in FIG. 3. Since the DNA fragment inserted in pGA22 has the same cleavage sites for restriction endonucleases as the cloned DNA fragment containing *Escherichia coli* operon (Cossart, P. et al.: Molec. Gen. Genet., 175, 39, 1979), it is clear that pGH2 has a the threonine operon.

(2) In vitro recombination of pCG11 and pGH2
pCG11 and pGH2 are completely digested with BglII and BamHI respectively by the same method as in Example 2 (2). Both digests containing 2 μg each of the plasmid DNAs are mixed. Then, 40 μl of T4 ligase buffer solution, 40 μl of ATP (5 mM), 0.2 μl of T4 ligase and 120 μl of H₂O are added to the whole mixture (200 μl). Reaction is carried out at 12° C. for 16 hours. The reaction mixture is extracted twice with 400 μl of phenol saturated with TES buffer solution and subjected to dialysis against TES buffer solution to remove phenol.

(3) Recovery of plasmid pEthrl
Protoplasts of *Corynebacterium glutamicum* LA 201 which is a derivative strain of the LA 103 strain and requires homoserine and leucine are transformed using, as a donor DNA, 100 μl of a mixture of a two-fold concentrated TSMC buffer solution and the ligase reaction mixture prepared above (1 : 1) in the same manner as in Example 1 (3). The transformants are spread on the RCGP agar medium and culturing is carried out at 30° C. for 6 days to regenerate the transformants. Cells grown over the whole surface of the agar medium are scraped, washed with physiological saline solution and subjected to centrifugation. The cells are again spread on a minimum agar medium M1 (pH 7.2) consisting of 10 g/l glucose, 1 g/l NH₄H₂PO₄, 0.2 g/l KCl, 0.2 g/l MgSO₄. 7H₂O, 10 mg/l FeSO₄. 7H₂O, 0.2 mg/l MnSO₄.(4–6)H₂O, 0.9 mg/l ZnSO₄. 7H₂O, 0.4 mg/l CuSO₄. 5H₂O, 0.09 mg/l Na₂B₄O₇. 10H₂O, 0.04 mg/l (NH₄)₆Mo₇O₂₄. 4H₂O, 50 μg/l biotin, 2.5 mg/l p-amino-benzoic acid, 1 mg/l thiamine hydrochloride and 16 g/l agar and containing 50 μg/ml leucine. Culturing is carried out at 30° C. for 3 days. Colonies formed are subjected to selection on an NB agar medium containing 12.5 μg/ml kanamycin and 100 μg/ml spectinomycin. Three strains selected at random are grown in 400 ml of the NB medium to an OD value of about 0.8. Cells are recovered and the plasmids are isolated from the cells by ethidium bromide-cesium chloride density gradient centrifugation described in Example 1 (1) whereby 40 to 55 μg of plasmid DNA is recovered from each strain.

These plasmid DNAs are digested with restriction endonucleases and analyzed by agarose gel electrophoresis as in Example 1 (3) to determine the molecular weights and cleavage sites for PstI, EcoRI and XhoI. The plasmid obtained from one strain is named pEthrl and the structure is illustrated in FIG. 3. It is confirmed that pEthrl has the structure wherein a BamHI fragment containing pGH2 threonine operon is combined with pCG11. One of the remaining strains has the same plasmid as pEthrl and the other has a plasmid wherein the BamHI fragment containing pGH2 threonine operon is combined at the opposite orientation.

*Corynebacterium glutamicum* LA 103 strain is again transformed with these plasmid DNAs as mentioned above. As a result, strains which do not require homoserine are obtained with high frequency, about 10⁻³ cell-/regenerated cell. All of them are endowed with the phenotypes of the resistance to kanamycin and spectinomycin and have the same plasmid as the donor plasmid characterized by the cleavage pattern for various restriction endonucleases.

EXAMPLE 5

Cloning of a DNA fragment with insertional inactivation

In this example, the possibility of detecting recombinant plasmids of pCE54 vector by the insertional inactivation of a gene responsible for a drug resistance is investigated. Plasmid pCG4 isolated from *Corynebacterium glutamicum* 225-250 (FERM P-5939, ATCC 31830) in the same manner as in the isolation of pCG2 in Example 1 (1) is used as a donor DNA. Plasmid pCG4 has a molecular weight of 29 Kb and is cleaved with EcoRI into 4 fragments.

2 units of EcoRI (product of Takara Shuzo Co., 4 units/ml) is added to 50 μl of an EcoRI reaction buffer solution (pH 7.5) consisting of 100 mM Tris-HCl, 7 mM MgCl$_2$, 50 mM NaCl and 7 mM 2-mercaptoethanol and containing 0.5 μg each of pCE54 obtained in Example 1 and pCG4 mentioned above. The mixture is allowed to react at 37° C. for 60 minutes and is then heated at 65° C. for 10 minutes to stop the reaction. Then, 10 ml of the T4 ligase buffer solution, 10 μl of ATP (5mM), 0.2 μl of T4 ligase and 30 μl of water are added to the reaction and the mixture is allowed to react at 12° C. for 16 hours. The mixture is extracted twice with 100 μl of phenol saturated with TES buffer solution and subjected to dialysis against TES buffer solution to remove phenol. Corynebacterium glutamicum LA 103 is transformed using 100 μl of a mixture (1:1) of two-fold concentrated TSMC buffer solution and the ligase reaction mixture mentioned above by the same method as in Example 1 (3), and kanamycin-resistant strains are selected. Fifty colonies formed are picked up at random and replica-plated on NB agar medium containing 6.25 μg/ml chloramphenicol, 1.6 μg/ml tetracycline and 12.5 μg/m kanamycin. Culturing is carried out at 30° C. for 3 days to determine the sensitivity of the strains. Eleven strains are resistant to tetracycline and kanamycin but are sensitive to chloramphenicol. The plasmids in 10 strains among the 11 strains are isolated by ethidium bromide-cesium chloride density gradient centrifugation as described in Example 1 (1).

These plasmid DNAs are digested with EcoRI and subjected to agarose electrophoresis. Since all the plasmids have higher molecular weights than that of pCE54 and the increased mass corresponds to the size of either of the four fragments formed by the digestion of pCG4 with EcoRI, it is confirmed that the recombinant plasmid contains these DNA fragments at the EcoRI cleavage site present in the gene responsible for the resistance to chloramphenicol of pCE54.

What is claimed is:

1. A recombinant vector plasmid which is constructed by introducing a DNA fragment containing an Eschcrichia coli, Bacillus or Staphylococcus gene into a plasmid autonomously replicable in and derived from a microorganism belonging to the genus Corynebacterium or Brevibacterium, wherein said recombinant vector plasmid is replicable in said microorganism belonging to the genus Corynebacterium or Brevibacterium and is detectable in said microorganism by expression of the phenotype of said introduced gene.

2. The recombinant vector plasmid according to claim 1, wherein the microorganism is a Corynebacterium glutamicum.

3. The recombinant vector plasmid according to claim 2, wherein the microorganism is Corynebacterium glutamicum 225-57, ATCC 31808, FERM P-5865; or Corynebacterium glutamicum 225-218, ATCC 31832, FERM P-5954.

4. Plasmid pCE54, or a plasmid constructed from plasmid pCE54 by deleting a DNA region from said plasmid which does not affect its function to replicate and its resistance to antibiotics or by inserting a foreign DNA fragment into said plasmid.

5. Plasmid pCB101, or a plasmid constructed from the plasmid pCB101 by deleting a DNA region from said plasmid which does not affect its function to replicate and its resistance to antibiotics or by inserting a foreign DNA fragment into said plasmid.

6. Plasmid pEthrl, or a plasmid constructed from the plasmid pEthrl by deleting a DNA region from said plasmid which does not affect its function to replicate and its resistance to antibiotics or by inserting a foreign DNA fragment into said plasmid.

7. A microorganism belonging to the genus Corynebacterium or Brevibacterium harboring the recombinant vector plasmid defined in claim 1.

8. The microorganism according to claim 7 wherein said microorganism is Corynebacterium glutamicum.

9. The recombinant vector plasmid according to claim 1, wherein said gene is an Escherichia coli gene.

* * * * *

UNITED STATES PATENT AND TRADEMARK OFFICE
CERTIFICATE OF CORRECTION

PATENT NO. : 4,710,471

DATED : December 1, 1987

INVENTOR(S) : RYOICHI KATSUMATA, ET AL.

Page 1 of 3

It is certified that error appears in the above-identified patent and that said Letters Patent is hereby corrected as shown below:

COLUMN 1

Line 53, ""Am ® gene" and "Tc ® gene"" should read --"$Am^R$ gene" and "$Tc^R$ gene"--.

Line 59, "Am ® gene" should read --$Am^R$ gene--.

Line 60, "Tc ® gene" should read --$Tc^R$ gene--.

COLUMN 2

Line 9, ""Cm ® gene" and Km ® gene"" should read --"$Cm^R$ gene" and $Km^R$ gene"--.

Line 10, "Am ® gene and Tc ® gene" should read --$Am^R$ gene and $Tc^R$ gene--.

Line 11, "Cm ® gene" should read --$Cm^R$ gene--.

Line 12, "Km ® gene" should read --$Km^R$ gene--.

Line 13, "Am ® gene and Tc ®" should read --$Am^R$ gene and $Tc^R$--.

Line 37, "Escherichra coli" should read --Escherichia coli--.

COLUMN 3

Line 21, "llustrate" should read --illustrate--.

COLUMN 4

Line 52, "Am ® gene" should read --$Am^R$ gene--.

UNITED STATES PATENT AND TRADEMARK OFFICE
CERTIFICATE OF CORRECTION

PATENT NO. : 4,710,471

DATED : December 1, 1987

INVENTOR(S) : RYOICHI KATSUMATA, ET AL.

It is certified that error appears in the above-identified patent and that said Letters Patent is hereby corrected as shown below:

COLUMN 5

Line 38, "<400" should read --> 400 --.

COLUMN 6

Line 25, "Km ® gene" should read --$Km^R$ gene--.
Line 40, "Km ® gene" should read --$Km^R$ gene--.

COLUMN 7

Line 20, "Km ® gene" should read --$Km^R$ gene--.
Line 27, "Km ® gene" should read --$Km^R$ gene--.

COLUMN 8

Line 65, "Eschericia coli" should read --Escherichia coli--.

COLUMN 10

Line 55, "$MgCl_26H_2O$," should read --$MgCl_2 \cdot 6H_2O$,--.
Line 57, "$Na_2B_4O_710H_2O$," should read --$Na_2B_4O_7 \cdot 10H_2O$,--.

COLUMN 12

Line 2, "0.14 g/l $MgCl_26H_2O$," should read --0.41 g/l $MgCl_2 \cdot 6H_2O$,--.
Line 3, "$MnSo_4(4-6)H_2O$," should read --$MnSo_4 \cdot (4-6)H_2O$,--.

UNITED STATES PATENT AND TRADEMARK OFFICE
CERTIFICATE OF CORRECTION

PATENT NO. : 4,710,471

DATED : December 1, 1987

INVENTOR(S) : RYOICHI KATSUMATA, ET AL.

It is certified that error appears in the above-identified patent and that said Letters Patent is hereby corrected as shown below:

COLUMN 12 (continued)

Line 3, "$ZnSo_4\ 7H_2O$," should read --$ZnSo_4 \cdot 7H_2O$,--.

Line 4, "$(NH_4)_6Mo.7O_{24}\ 4H_2O$," should read --$(NH_4)_6Mo_7O_{24} \cdot 4H_2O$,--.

COLUMN 18

Line 3, "Eschcrichia coli," should read --Escherichia coli,--.

Signed and Sealed this

Seventeenth Day of May, 1988

Attest:

DONALD J. QUIGG

*Attesting Officer*

*Commissioner of Patents and Trademarks*